United States Patent [19]

Nguyen Than et al.

[11] Patent Number: 5,889,187

[45] Date of Patent: *Mar. 30, 1999

[54] CATALYTIC HYDROGENATION PROCESS AND A CATALYST FOR USE IN THE PROCESS

[75] Inventors: Canh Nguyen Than, La Celle Saint Cloud; Blaise Didillon; Patrick Sarrazin, both of Rueil Malmaison; Charles Cameron, Paris, all of France

[73] Assignee: Institut Francais du Petrole, France

[ * ] Notice: The term of this patent shall not extend beyond the expiration date of Pat. No. 5,648,576.

[21] Appl. No.: 808,649

[22] Filed: Feb. 28, 1997

Related U.S. Application Data

[62] Division of Ser. No. 466,685, Jun. 6, 1995, Pat. No. 5,648,576.

[30] Foreign Application Priority Data

| Jun. 9, 1994 | [FR] | France | 94/07 .044 |
| Jun. 9, 1994 | [FR] | France | 94/07 .045 |

[51] Int. Cl.⁶ .............. C07C 5/09; B01J 21/04; B01J 23/58; B01J 23/44
[52] U.S. Cl. ............ 585/260; 585/259; 502/328
[58] Field of Search ............ 585/259, 260; 502/328

[56] References Cited

U.S. PATENT DOCUMENTS

| 2,620,314 | 12/1952 | Hoekstra | 252/448 |
| 3,651,167 | 3/1972 | de Rosset | 260/681.5 |
| 3,912,789 | 10/1975 | Frevel et al. | 585/259 |
| 4,061,598 | 12/1977 | Makar | 252/466 |
| 4,247,725 | 1/1981 | Ohmori et al. | 585/259 |
| 4,404,124 | 9/1983 | Johnson et al. | 252/466 |
| 4,547,600 | 10/1985 | Cosyns et al. | 585/259 |
| 4,822,936 | 4/1989 | Maurer et al. | 585/259 |
| 4,906,602 | 3/1990 | Schneider et al. | 502/304 |
| 5,059,731 | 10/1991 | Berrebi | 502/259 |
| 5,250,487 | 10/1993 | Wirtz et al. | 502/243 |

FOREIGN PATENT DOCUMENTS

| 0 064 301 | 11/1982 | European Pat. Off. . |
| 0 124 744 | 11/1984 | European Pat. Off. . |
| 0 519 436 | 12/1992 | European Pat. Off. . |
| 1 177 764 | 4/1959 | France . |
| 2 338 076 | 8/1977 | France . |

Primary Examiner—Bekir L. Yildirim
Attorney, Agent, or Firm—Millen, White, Zelano, & Branigan, P.C.

[57] ABSTRACT

A process for the selective hydrogenation in the gas phase of acetylene compounds containing 2 or 3 carbon atoms to the corresponding ethylene compounds is described. The process uses a catalyst in the form of spherules or extrudates containing palladium, at least one group IB metal, optionally at least one alkaline or alkaline-earth metal and alumina, in which at least 80% of the palladium and at least 80% of the group IB element are present in a volume at the periphery of the catalyst defined between a spherical or cylindrical surface of radius $r_1$ corresponding to the average spherule or extrudate diameter and a spherical or cylindrical surface of radius $r_2$ at least equal to $0.8r_1$. More particularly, the catalyst comprises an alumina, palladium in a proportion of 0.01% to 0.5% by weight, and group IB metal in a proportion of 0.001 to 0.02% by weight, with a weight ratio of group IB metal/palladium of 0.05 to 0.25.

15 Claims, 2 Drawing Sheets

CATALYTIC HYDROGENATION PROCESS AND A CATALYST FOR USE IN THE PROCESS

This is a continuation, division, of the application Ser. No. 08/466,685 filed Jun. 6,1995 now Pat. No. 5,648,576

BACKGROUND OF THE INVENTION

The invention concerns a process for the selective hydrogenation in the gas phase of acetylene hydrocarbons containing 2 or 3 carbon atoms (acetylene or propyne) to the corresponding ethylenic hydrocarbons (ethylene or propylene).

Ethylene is a monomer used for the preparation of a large number of polymers. It is generally obtained by hydrocarbon pyrolysis or steam cracking processes. The ethylene produced contains small quantities of acetylene (generally less than 3%) which must be eliminated before use. The acetylene contents which are tolerated in ethylene for use in polymer production are generally less than 10 ppm, more often less than 5 ppm.

One of the techniques used to eliminate acetylene in ethylene is to selectively hydrogenate it to ethylene in the presence of a palladium based, catalyst supported on a refractory support such as alumina. The general problem with these monometallic catalysts (constituted solely by palladium supported on alumina) is that, when the operating conditions are such as to permit complete elimination of the acetylene, a portion of the ethylene is also converted to ethane. In addition, these monometallic catalysts generally have relatively low stabilities due to the formation of large amounts of oligomers which gradually cover the catalyst surface under the reaction conditions. This deposit of hydrocarbon can, of course, be eliminated by controlled oxidation processes, but it is of advantage in an industrial process to have as long a lifetime as possible for the catalyst between two regenerations.

The addition of enhancers to the palladium has frequently been proposed in order to improve catalyst properties. These additives can be, for example, silver (U.S. Pat. No. 2,802,889), and iron and silver (U.S. Pat. No. 3,243,387).

These enhancers can also be selected from alkaline or alkaline-earth metals such as lithium (U.S. Pat. No. 3,325,556), potassium (European patent application EP-A- 0 124 744) or calcium (U.S. Pat. No. 4,329,530).

Whether using monometallic catalysts (catalysts based on palladium alone) or enhanced catalysts (catalysts containing palladium and at least one other element), the skilled person knows that when the palladium is concentrated at the surface of the spherules of the catalyst, catalytic performance is substantially superior to that of a catalyst with an identical form in which the palladium is homogeneously distributed through the spherules of the catalyst. In the case of bimetallic palladium-silver formulations, for example, it has been discovered that when the palladium is situated at the periphery of the spherules of the catalyst and that the silver is homogeneously distributed, the catalyst has improved properties (U.S. Pat. No. 4,404,124; EP-A-0 064 301 and French patent FR-A-2 597 113), in particular as regards a lower degree of ethane and oligomerisation product formation.

Further, Japanese patent application JP-A-04 108 540 describes liquid phase selective hydrogenation catalysts for 1,3-butadiene, in which silver is precipitated on and supported by a palladium surface. In these catalysts, the support consists of alumina with a relatively high specific surface area and a Ag/Pd weight ratio of 0.3 to 5.0, preferably 0.5 to 3.0.

SUMMARY OF THE INVENTION

We have now surprisingly discovered that selective hydrogenation in the gas phase of acetylenic hydrocarbons containing 2 or 3 carbon atoms (acetylene or propyne) to the corresponding ethylenic hydrocarbons (ethylene or propylene) can be carried out using a catalyst in the form of spherules or extrudates containing palladium, at least one metal from group IB of the periodic classification, and alumina, in which a proportion of at least 80% of the palladium and at least 80% of the group IB metal are present in a volume at the periphery of the catalyst delimited by a spherical or cylindrical surface with radius $r_1$ corresponding to the average radius of the spherules or extrudates of the catalyst and a spherical or cylindrical surface with radius $r_2$ at least equal to $0.8r_1$. The silver/palladium weight ratio is between 0.05 and 0.4, preferably between 0.05 and 0.25.

When the catalyst is in the form of spherules or extrudates, $r_1$ and $r_2$ can be represented as follows:

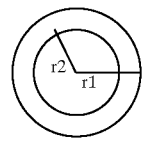

More particularly, the palladium content is between 0.01% and 0.5% by weight of catalyst. The group IB element is most frequently silver at a content of between 0.001% and 0.02% by weight.

The support used is an alumina, in particular an alpha alumina. It is usually used in the form of spherules with diameters generally of between 2 and 4 mm. The characteristics of the alumina are generally as follows: a specific surface area of between 5 and 150 $m^2/g$, preferably between 5 and 60 $m^2/g$; a pore volume of 0.3 to 0.95 $cm^3/g$ and a pore diameter of greater than 100 Å. These different characteristics are measured using analytical techniques which are known to the skilled person.

The palladium can be introduced, using techniques which are known to the skilled person, to distribute the palladium on the surface of the support spherules, with the criteria described above. Even distribution of the palladium can be verified using conventional techniques such as the Castaing microprobe. The palladium can, for example, be introduced by impregnation of an aqueous or organic solution of a palladium precursor. The precursor can, for example, be an inorganic compound such as palladium chloride, palladium nitrate, palladium tetrammine dihydroxide, palladium tetrammine chloride, or an organometallic compound such as palladium bis π allyl or palladium bis acetylacetonate.

The group IB element, in particular silver, is introduced in such a fashion that it remains concentrated at the periphery of the support spherules. Analysis of the silver content after controlled abrasion of the catalyst spherules ensures good distribution of the silver in the catalyst spherules. Silver nitrate is normally used as the precursor. Silver acetate, silver citrate, silver chloride or silver carbonate, for example, can also be used.

The process for the selective hydrogenation of acetylenic hydrocarbons containing 2 or 3 carbon atoms to the corresponding ethylenic hydrocarbons in the gas phase of the invention can also be carried out using a catalyst as described above, further containing at least one alkali or alkaline-earth metal.

The alkali or alkaline-earth metal content in the catalyst is advantageously selected so that the atomic ratio of alkali or alkaline-earth metal to palladium is between 2 and 20, preferably between 4 and 15. Preferably, this content is between 0.05% and 0.2% by weight of catalyst.

Sodium or potassium can be used as the alkali metal.

The alkali or alkaline-earth metal is introduced using techniques which are known to the skilled person. Nitrates, acetates, chlorides, carbonates and hydroxides are normally used as precursors.

The palladium and the group IB metal, and optionally the alkali or alkaline-earth metal, can be introduced by a common solution of precursors or by separate solutions each containing one or two elements. In the latter case, drying, calcining or reduction treatments effected at temperatures of between 120° C. and 900° C. can optionally be carried out between two successive impregnation steps.

When the palladium and group IB element (in particular silver) are introduced by different solutions, examples of the techniques which can be used are described, for example, in U.S. Pat. No. 4,533,779 which uses silver chloride as the precursor, or U.S. Pat. No. 4,504,593 which uses silver citrate as the precursor.

The catalyst obtained is generally dried at temperatures between room temperature and 150° C. The dried catalyst can be used as it is or, more often, it is preferably calcined to decompose the metallic precursors before use, or it can be reduced. Calcining is generally carried out by treating the catalyst in a stream of air at a temperature of between 400° C. and 900° C. Reduction can be carried out by treating the catalyst with a gas containing hydrogen at a temperature of between room temperature and 500° C.

The hydrogenation process of the invention is particular suitable for the hydrogenation of the acetylene present in a gas containing ethylene. In order to approach the reaction conditions which would completely eliminate the acetylene, the molar ratio of hydrogen to acetylene is generally between 1 and 2, the reaction temperature is generally between 25° C. and 100° C., and the pressure is generally between 1 and 5 MPa. The feed flow rate, expressed in litres of gaseous feed per litre of catalyst per hour, is generally between 1000 and 10 000 $h^{-1}$.

During use, the catalyst deactivates due to deposition of hydrocarbon compounds which gradually cover the active phase. When the performance of the catalyst is judged to be insufficient, the catalyst can be regenerated. Catalyst regeneration is effected by controlled combustion of the hydrocarbon species present on the catalyst. Combustion is carried out under conditions which are known to the skilled person, generally by heating the catalyst slowly in the presence of a gas containing oxygen at a temperature of between 350° C. and 500° C.

BRIEF DESCRIPTION OF THE DRAWINGS

The attached drawings are histograms showing the average distribution of the elements in the catalyst grains, with FIG. 1 being further explained in Example 1 and FIG. 2 being further explained in Example 8.

The following non limiting examples illustrate the invention Examples 3, 4, 10 and 11 are given by way of comparison.

EXAMPLE 1

Preparation of catalyst A (in accordance with the invention)

Figure 1:
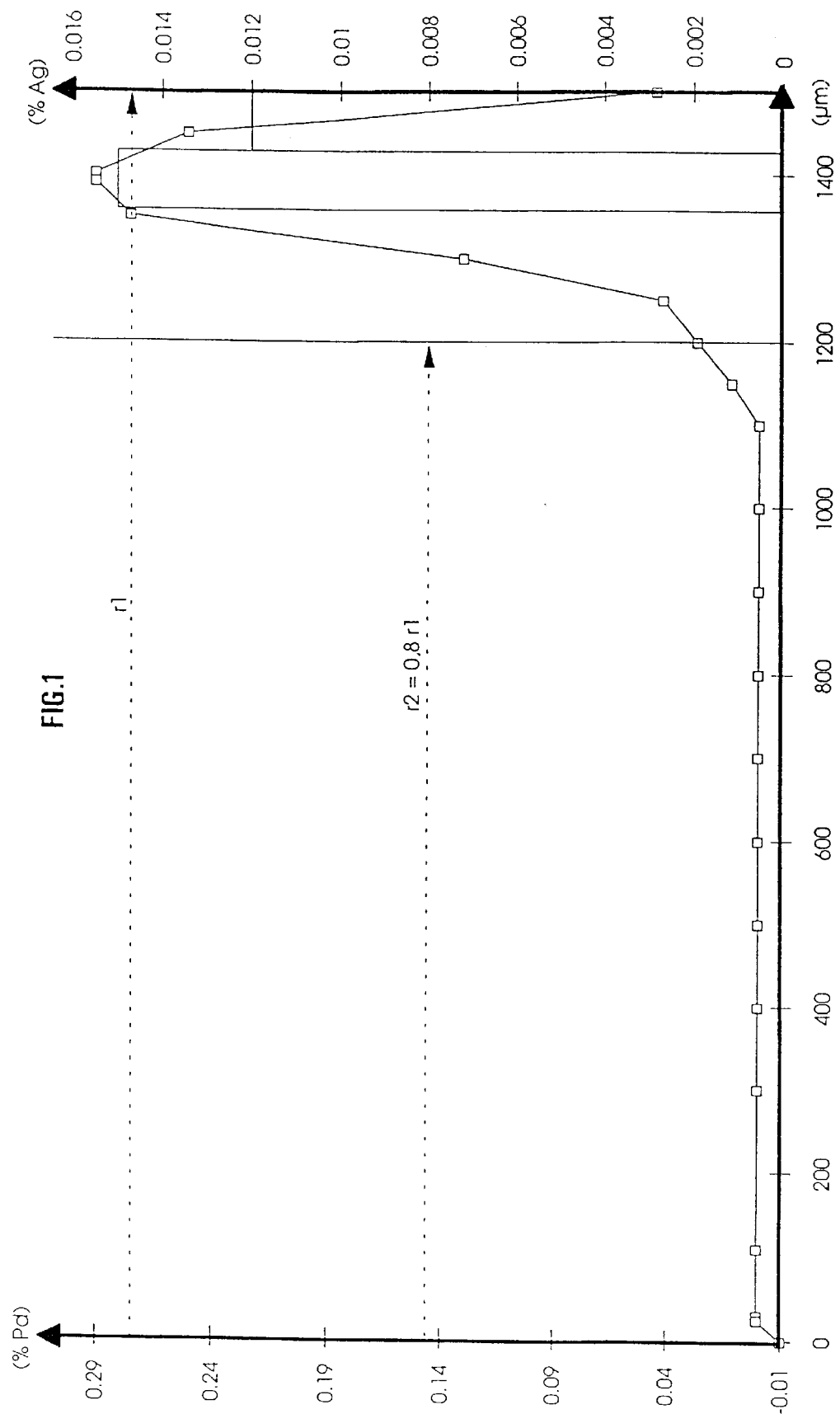

A catalyst in accordance with the invention (catalyst A) was prepared by impregnating 100 g of an alpha alumina based support with 60 ml of a solution of nitric acid, palladium nitrate and silver nitrate. The support was in the form of 2 to 4 mm diameter spherules with a specific surface area of 10 $m^2/g$ and a pore volume of 0.6 $cm^3/g$. After impregnation, the catalyst was dried at 120° C. and calcined in air at 750° C. Catalyst A produced contained 0.05% by weight of palladium and 0.005% by weight of silver. The average distribution of the elements in the catalyst grains is shown in FIG. 1. In this diagram, the abscissa shows the radius in micrometers and the ordinate shows the local concentration by weight of palladium on the left and the local concentration of silver on the right, shown in the form of a histogram.

These analyses show that 84% of the silver was concentrated in a volume delimited by a spherule of radius $r_1$ of 1.5 mm and a spherule of radius $r_2$ of 1.39 mm. The ratio $r_2/r_1$ is thus 0.93, i.e., much higher than 0.8. Regarding the palladium, 94% of the palladium was concentrated in a volume delimited by a spherule of radius $r_1$ of 1.5 mm and a spherule of radius $r_2$ of 1.2 mm. The ratio $r_2/r_1$ in this case was 0.8. The element distribution in the catalyst grain was thus well in accordance with the invention.

EXAMPLE 2

Preparation of catalyst B (in accordance with the invention)

A catalyst in accordance with the invention (catalyst B) was prepared by impregnating 100 g of an alpha alumina based support with 60 ml of a solution of nitric acid, palladium nitrate and silver nitrate. The support was in the form of 2 to 4 mm diameter spherules with a specific surface area of 10 $m^2/g$ and a pore volume of 0.6 $cm^3/g$. After impregnation, the catalyst was dried at 120° C. and calcined in air at 750° C. Catalyst B produced contained 0.05% by weight of palladium and 0.010% by weight of silver. The average distribution of the elements in the catalyst grains was in accordance with the invention.

EXAMPLE 3

Preparation of catalyst C (comparative)

Catalyst C was prepared using the same procedure as that of Example 1 but using an impregnating solution containing nitric acid and palladium nitrate. Catalyst C produced contained 0.05% of palladium. Analysis of catalysts A and C using a Castaing microprobe did not show any significant differences in the palladium distribution between the two samples.

EXAMPLE 4

Preparation of catalyst D (comparative)

Catalyst D was prepared by immersing 100 g of support in 120 ml of an aqueous solution of silver nitrate containing 8 mg of silver at room temperature. The catalyst was stirred for several minutes. The supernatant solution was eliminated. The catalyst was then dried at 120° C. and calcined at 500° C. The catalyst was impregnated with 60 ml of a solution of nitric acid and palladium nitrate. After impregnation, the catalyst was dried at 120° C. and calcined in air at 750° C. Catalyst D produced contained 0.05% by weight of palladium and 0.005% by weight of silver. Analysis using a Castaing microprobe of catalysts A and D did not show any significant differences in palladium distribution between the two samples. On the other hand, analysis of the silver content after controlled abrasion of the catalyst spherules did not identify any difference in silver concentration through the catalyst spherules.

EXAMPLE 5

Preparation of catalyst E (in accordance with the invention)

50 g of monometallic catalyst C was reduced in aqueous solution by citric acid. 4 mg of silver acetate was then introduced into this solution. The reaction system was gently stirred for 8 hours. The catalyst was then filtered, dried for 16 hours at 120° C. and calcined for 2 hours at 750° C. Catalyst A produced contained 0.05% by weight of palladium and 0.005% by weight of silver. The average distribution of elements in the grains of catalyst E was in accordance with the invention.

EXAMPLE 6

Comparison of the hydrogenating properties of the different catalysts.

Catalytic tests were carried out on catalysts A, B, C, D and E to determine their selectivity and stability during the hydrogenation of acetylene contained in a feed containing 98% of ethylene and 2% of acetylene. 15 ml of the catalyst to be tested was placed in a vertical steel reactor. The reactor was then placed in a furnace to control the temperature. The catalyst was reduced in a hydrogen stream at 150° C. for two hours at atmospheric pressure. The temperature was then raised to 50° C., with a hydrogen flow rate of 1.5 $l.h^{-1}$ and a pressure of 2.5 MPa. The feed, composed of 98% of ethylene and 2% of acetylene, was then injected at a volume flow rate corresponding to a space velocity of 3300 $h^{-1}$. Analysis of the gaseous effluent leaving the reactor was effected by gas phase chromatography. Under these conditions, the stability of the catalyst is defined as the time after which acetylene is detected at the reactor outlet. The selectivity of the catalyst corresponded to the ethylene content in the feed after total elimination of the acetylene. The results obtained are shown in Table I.

TABLE 1

Comparison of performances of catalysts A, B, C, D and E during hydrogenation of acetylene.

| Catalysts | Catalyst stability (hours) | Catalyst selectivity (%) |
| --- | --- | --- |
| Catalyst A (inventive) | 96 | 98.5 |
| Catalyst B (inventive) | 85 | 98.5 |
| Catalyst C (comparative) | 22 | 98.3 |
| Catalyst D (comparative) | 36 | 98.2 |
| Catalyst E (inventive) | 94 | 98.5 |

These results clearly show that the catalysts of the invention (catalysts A, B and E) have better catalytic performances (stability and selectivity) than those of monometallic catalysts (catalyst C) or those in which the silver is uniformly distributed in the spherules of catalyst (catalyst D).

EXAMPLE 7

Regeneration of a catalyst in accordance with the invention

After using catalyst A for 120 hours under the conditions of Example 6, catalyst A was regenerated. In the regeneration procedure, the catalyst was heated to 200° C. in nitrogen, then treated in diluted air at a temperature of between 200° C. and 500° C. to burn off the hydrocarbon compounds present on the catalyst.

After regeneration, the performances of the regenerated catalyst A were evaluated under the conditions of Example 6. The performances of such a regenerated system are shown in Table 2.

TABLE 2

| Catalysts | Catalyst stability (hours) | Catalyst selectivity (%) |
| --- | --- | --- |
| Catalyst A (inventive) | 96 | 98.5 |
| Catalyst A (regenerated) | 95 | 98.7 |

These results show that, within experimental error, regenerated catalyst A had the same acetylene hydrogenation performances as the new catalyst.

EXAMPLE 8

Preparation of catalyst F (in accordance with the invention).

Figure 2:
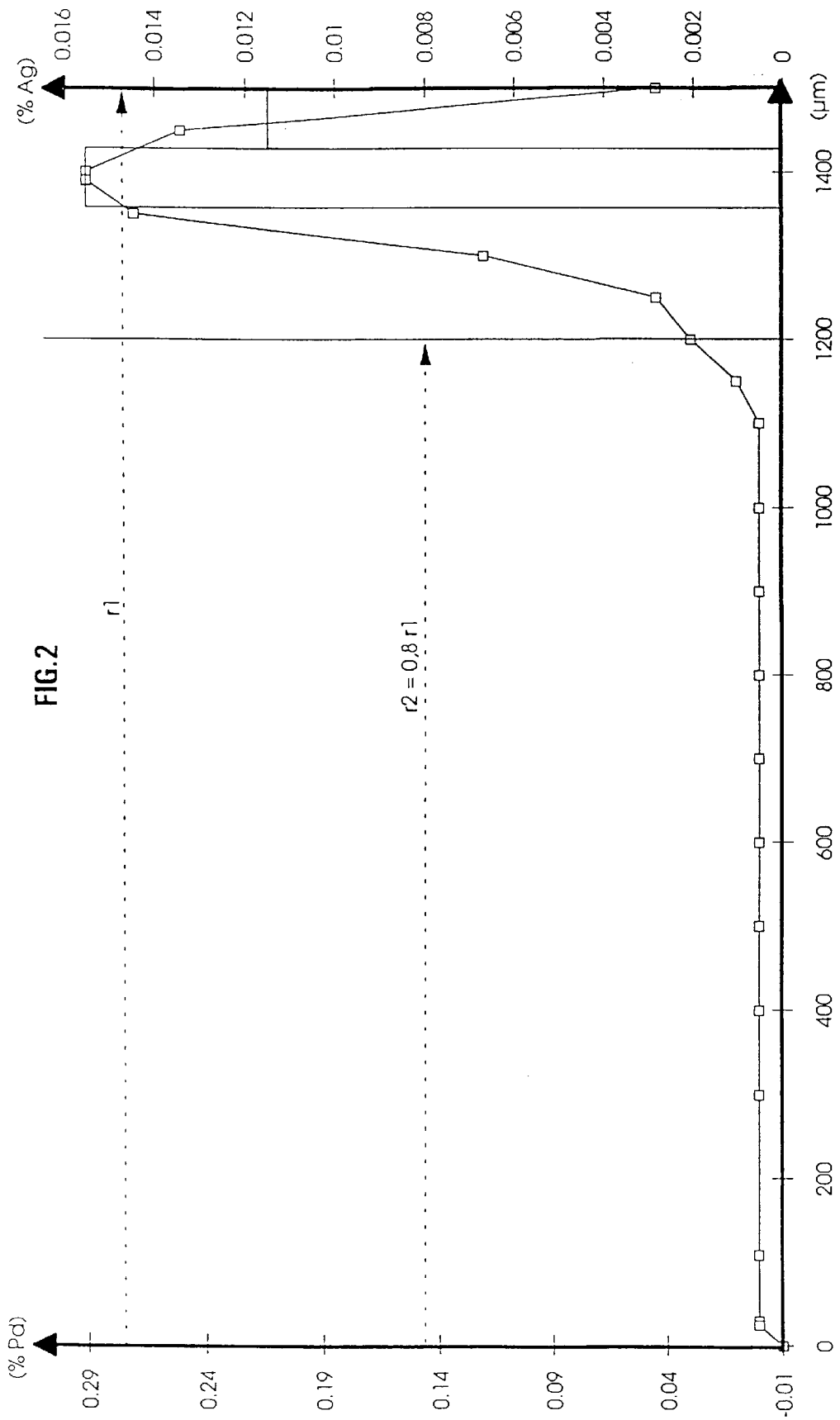

A catalyst in accordance with the invention (catalyst F) was prepared by impregnating 100 g of an alpha alumina based support with 60 ml of a solution of nitric acid, palladium nitrate, silver nitrate and sodium nitrate. The support was in the form of 2 to 4 mm diameter spherules with a specific surface area of 10 $M^2/g$ and a pore volume of 0.6 $cm^3/g$. After impregnation, the catalyst was dried at 120° C. and calcined in air at 750° C. Catalyst F produced contained 0.05% by weight of palladium, 0.005% by weight of silver and 0.05% of sodium. The average distribution of the elements in the catalyst grains is shown in FIG. 2.

In this diagram, the abscissa shows the radius in micrometers and the ordinate shows the local concentration by weight of palladium represented by the symbols (C) on the left, and the local concentration of silver on the right, shown in the form of a histogram.

These analyses showed that 84% of the silver was concentrated in a volume delimited by a spherule of radius $r_1$ of 1.5 mm and a spherule of radius $r_2$ of 1.39 mm. The ratio $r_2/r_1$ was thus 0.93, i.e., much higher than 0.8. Regarding the palladium, 94% of the palladium was concentrated in a volume delimited by a spherule of radius $r_1$ of 1.5 mm and a spherule of radius $r_2$ of 1.2 mm. The ratio $r_2/r_1$ in this case was 0.8. The elemental distribution in the catalyst grain was thus well in accordance with the invention.

EXAMPLE 9

Preparation of catalyst G (in accordance with the invention).

A catalyst in accordance with the invention (catalyst G) was prepared by impregnating 100 g of an alpha alumina based support with 60 ml of a solution of nitric acid, palladium nitrate, silver nitrate and sodium nitrate. The support was in the form of 2 to 4 mm diameter spherules with a specific surface area of 10 $m^2/g$ and a pore volume of 0.6 $cm^3/g$. After impregnation, the catalyst was dried at 120° C. and calcined in air at 750° C. Catalyst G produced contained 0.05% by weight of palladium, 0.010% by weight of silver and 0.05% of sodium. The average distribution of the elements in the catalyst grains was in accordance with the invention.

EXAMPLE 10

Preparation of catalyst H (comparative)

Catalyst H was prepared using the same procedure as that of Example 8 but using an impregnating solution containing nitric acid, palladium nitrate and sodium nitrate. Catalyst H produced contained 0.05% of palladium and 0.05% of sodium. Analysis of catalysts F and H using a Castaing microprobe did not show any significant differences in palladium distribution between the two samples.

EXAMPLE 11

Preparation of catalyst I (comparative)

Catalyst I was prepared by immersing 100 g of support in 120 ml of an aqueous solution of silver nitrate containing 8 mg of silver at room temperature. The catalyst was stirred for several minutes. The supernatant solution was eliminated. The catalyst was then dried at 120° C. and calcined at 500° C. The catalyst was impregnated with 60 ml of a solution of nitric acid, palladium nitrate and sodium nitrate. After impregnation, catalyst I produced contained 0.05% by weight of palladium, 0.005% by weight of silver and 0.05% of sodium. Analysis using a Castaing microprobe of catalysts F and I did not show any significant differences in palladium distribution between the two samples. On the other hand, analysis of the silver content after controlled abrasion of the catalyst spherules did not identify any differences in silver concentration through the catalyst spherules.

EXAMPLE 12

Preparation of catalyst J (in accordance with the invention).

A catalyst in accordance with the invention (catalyst J) was prepared by impregnating 100 g of an alpha alumina based support with 60 ml of a solution of nitric acid, palladium nitrate, silver nitrate and sodium nitrate. The support was in the form of 2 to 4 mm diameter spherules with a specific surface area of 10 $m^2/g$ and a pore volume of 0.6 $cm^3/g$. After impregnation, the catalyst was dried at 120° C. and calcined in air at 750° C. Catalyst J produced contained 0.05% by weight of palladium, 0.020% of silver and 0.05% of sodium. The average distribution of the elements in the catalyst grains was in accordance with the invention.

EXAMPLE 13

Preparation of catalyst K (in accordance with the invention).

A catalyst in accordance with the invention (catalyst K) was prepared by impregnating 100 g of an alpha alumina based support with 60 ml of a solution of nitric acid, palladium nitrate, silver nitrate and sodium nitrate. The support was in the form of 2 to 4 mm diameter spherules with a specific surface area of 10 $m^2/g$ and a pore volume of 0.6 $cm^3/g$. After impregnation, the catalyst was dried at 120° C. and calcined in air at 750° C. Catalyst K produced contained 0.05% by weight of palladium, 0.010% of silver and 0.1% of sodium. The average distribution of the elements in the catalyst grains was in accordance with the invention.

EXAMPLE 14

Comparison of the hydrogenating properties of the different catalysts.

Catalytic tests were carried out on catalysts F, G, H, I, J and K to determine their selectivity and stability during the hydrogenation of acetylene contained in a feed containing 98% of ethylene and 2% of acetylene.

15 ml of the catalyst to be tested was placed in a vertical steel reactor. The reactor was then placed in a furnace to control the temperature. The catalyst was reduced in a hydrogen stream at 150° C. for two hours at atmospheric pressure. The temperature was then raised to 50° C., with a hydrogen flow rate of 1.5 $l.h^{-1}$ and a pressure of 2.5 MPa. The feed, composed of 98% of ethylene and 2% of acetylene, was then injected at a volume flow rate corresponding to a space velocity of 3300 $h^{-1}$. Analysis of the gaseous effluent leaving the reactor was effected by gas phase chromatography. Under these conditions, the stability of the catalyst was defined as the time after which acetylene was detected at the exit to the reactor. The selectivity of the catalyst corresponded to the ethylene content in the feed after total elimination of the acetylene. The results obtained are shown in Table 3.

TABLE 3

Comparison of performances of catalysts F, G, H, I, J and K during hydrogenation of acetylene.

| Catalysts | Catalyst stability (hours) | Catalyst selectivity (%) |
| --- | --- | --- |
| Catalyst F (inventive) | 105 | 98.2 |
| Catalyst G (inventive) | 120 | 98.3 |
| Catalyst H (comparative) | 65 | 98.3 |
| Catalyst I (comparative) | 66 | 98.2 |
| Catalyst J (inventive) | 101 | 98.3 |
| Catalyst K (inventive) | 121 | 98.7 |

These results clearly show that the catalysts of the invention (catalysts F, G, J or K) have better catalytic performances (stability and selectivity) than those of monometallic catalysts (catalyst H) or those in which the silver is uniformly distributed in the spherules of catalyst (catalyst I).

EXAMPLE 15

Regeneration of a catalyst in accordance with the invention

After using catalyst F for 120 hours under the conditions of Example 14, catalyst F was regenerated. In the regeneration procedure, the catalyst was heated to 200° C. under nitrogen, then treated in diluted air at a temperature of between 200° C. and 500° C. to burn off the hydrocarbon compounds present on the catalyst.

After regeneration, the performances of the regenerated catalyst F were evaluated under the conditions of Example 14. The performances of such a regenerated system are shown in Table 4.

TABLE 4

| Catalysts | Catalyst stability (hours) | Catalyst selectivity (%) |
| --- | --- | --- |
| Catalyst F (inventive) | 105 | 98.5 |

TABLE 4-continued

| Catalysts | Catalyst stability (hours) | Catalyst selectivity (%) |
|---|---|---|
| Catalyst F (regenerated) | 104 | 98.7 |

These results show that, within experimental error, regenerated catalyst F had the same acetylene hydrogenation performances as the new catalyst.

We claim:

1. A process for the selective hydrogenation in the gas phase of acetylenic hydrocarbons containing 2 or 3 carbon atoms to the corresponding ethylenic hydrocarbons, comprising passing a gaseous feed comprising at least one acetylenic hydrocarbon containing 2 or 3 carbon atoms in the presence of hydrogen over a catalyst in the form of spherules or extrudates containing palladium, at least one metal from group IB of the periodic classification, and alumina, the weight ratio of group IB metal to palladium being 0.05 to 0.4, a proportion of at least 80% of the palladium and at least 80% of the group IB metal being present in a volume at the periphery of the catalyst which is delimited by a spherical or cylindrical surface with radius $r_1$ corresponding to the average radius of the spherules or extrudates of the catalyst and a spherical or cylindrical surface with radius $r_2$ at least equal to $0.8r_1$.

2. The process according to claim 1, wherein
   said alumina has a specific surface area of 5 to 150 $m^2/g$; and
   the palladium content is 0.01% to 0.5% by weight.

3. A process according to claim 1 wherein the alumina has a specific surface area of 5 to 60 $m^2/g$.

4. A process according to claim 1, wherein the group IB metal is silver.

5. A process according to claim 1, wherein the catalyst further contains at least one alkali or alkaline-earth metal.

6. A process according to claim 5, wherein, in the catalyst, the atomic ratio of alkali or alkaline-earth metal to palladium is 2 to 20.

7. A process according to claim 5, wherein the alkali or alkaline-earth metal content in the catalyst is 0.05% to 0.2% by weight.

8. A process according to claim 2, wherein the group IB metal is silver.

9. A process according to claim 3, wherein the group IB metal is silver.

10. A process according to claim 5, wherein the group IB metal is silver.

11. A process according to claim 6, wherein the group IB metal is silver.

12. A process according to claim 7, wherein the group IB metal is silver.

13. A process according to claim 1, wherein the palladium content is 0.01% to 0.5% by weight.

14. A process according to claim 13, wherein the Group IB metal is silver.

15. The process according to claim 1, wherein said alumina has a specific surface area of 5 to 150 $m^2/g$; and the group IB metal content is 0.001% to 0.02% by weight.

* * * * *